United States Patent [19]

Heidebrecht

[11] Patent Number: 4,824,989

[45] Date of Patent: Apr. 25, 1989

[54] RECOVERY PROCESS

[75] Inventor: Gary D. Heidebrecht, Orangeburg, S.C.

[73] Assignee: Ethyl Corporation, Richmond, Va.

[21] Appl. No.: 21,162

[22] Filed: Mar. 3, 1987

[51] Int. Cl.$^4$ .................. C07C 121/62; C07C 69/76
[52] U.S. Cl. .................. 558/423; 558/376; 558/425; 560/100
[58] Field of Search .............. 558/376, 423, 425; 560/100; 423/42

[56] References Cited

U.S. PATENT DOCUMENTS 4,439,617  3/1984  Sestans et al. ............ 558/415 X
4,590,010  5/1986  Ramachandran et al. ...... 558/341

OTHER PUBLICATIONS

Matsui, et al., "Chem. Letters", (1981), pp. 1719–1720, Chemistry Society of Japan.

Primary Examiner—Joseph Paul Brust
Attorney, Agent, or Firm—Patricia J. Hogan

[57] ABSTRACT

A (trifluoromethyl)naphthalene which has been prepared by reacting a halonaphthalene with a trifluoroacetate salt in the presence of cuprous iodide and a dipolar aprotic solvent is recovered by (1) replacing the dipolar aprotic solvent in the final reaction mixture with an alkane containing 6–12 carbons, (2) heating the resultant slurry to a temperature sufficient to dissolve the organic ingredients, (3) allowing the inorganic ingredients of the slurry to settle, (4) decanting the organic layer, and (5) cooling to precipitate the (trifluoromethyl)naphthalene.

11 Claims, No Drawings

RECOVERY PROCESS

FIELD OF THE INVENTION

This invention relates to (trifluoromethyl)naphthalenes and more particularly to a process for recovering them.

BACKGROUND

As disclosed in U.S. Pat. No. 4,590,010 (Ramachandran et al.) and copending applications Ser. No. 808,304 (Lin et al.), filed Dec. 12, 1985, and Ser. Nos. 854,084 (Davidson I) and 854,085 (Davidson II), filed Apr. 21, 1986, it is known that (trifluoromethyl)naphthalenes can be prepared by reacting a corresponding halonaphthalene with a trifluoroacetate salt in the presence of cuprous iodide and a dipolar aprotic solvent. The products of these reactions can be recovered by conventional techniques involving filtration and centrifugation, but such recovery processes have proved to be unsatisfactory. What is needed is a recovery process which separates the trifluoromethylated product from the other ingredients of the synthesis mixture without the need for a troublesome filtration step and which accomplishes the separation in such a way as to facilitate recycling of the solvent and cuprous iodide.

SUMMARY OF INVENTION

An object of this invention is to provide a novel process for recovering a (trifluoromethyl)naphthalene from a synthesis mixture obtained by reacting a halonaphthalene with a trifluoroacetate salt in the presence of cuprous iodide and a dipolar aprotic solvent.

Another object is to provide such a process which facilitates recycling of the solvent and cuprous iodide.

These and other objects are attained by (1) replacing the dipolar aprotic solvent in the aforementioned synthesis mixture with an alkane containing 6–12 carbons, (2) heating the resultant slurry to a temperature sufficient to dissolve the organic ingredients, (3) allowing the inorganic ingredients of the slurry to settle, (4) decanting the organic layer, and (5) cooling to precipitate the (trifluoromethyl)naphthalene.

DETAILED DESCRIPTION

The synthesis mixture which is subjected to the process of the invention is a (trifluoromethyl)naphthalene reaction mixture obtained by reacting a halonaphthalene corresponding to the formula:

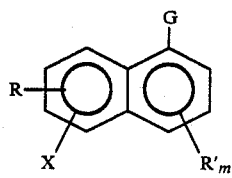

with a trifluoroacetate salt in the presence of cuprous iodide and a dipolar aprotic solvent to form a (trifluoromethyl)naphthalene corresponding to the formula:

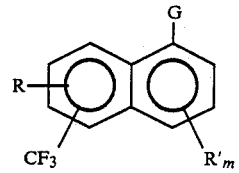

in which formulas X is bromo or iodo, R and R' are independently selected from alkyl and alkoxy groups containing 1–6 carbons, m is 0 or 1, and G is —CN or —COOR" in which R" is saturated hydrocarbyl. Such synthesis mixtures and their preparation are taught in Ramachandran et al., Lin et al., and Davidson I and II, the teachings of all of which are incorporated herein in toto by reference.

As indicated in these references, the synthesis mixtures wherein the (trifluoromethyl)naphthalene is a 6-alkoxy-5-trifluoromethyl-1-cyanonaphthalene, such as 6-methoxy-5-trifluoromethyl-1-cyanonaphthalene, or a 6-alkoxy-5-trifluoromethyl-1-naphthoate, such as methyl 6-methoxy-5-trifluoromethyl-1-naphthoate, are of particular interest because of their utility in the preparation of tolrestat-type pharmaceuticals. Moreover, in the preparation of these and similar compounds, iodo precursors have a yield advantage and bromo precursors an economic advantage, while potassium and tetraalkylammonium salts are preferred over sodium salts, and potassium salts are particularly preferred. Also, although N,N-dimethylformamide and N,N-dimethylacetamide are preferred solvents, other dipolar aprotic solvents, such as N-methylpyrrolidone, hexamethylphosphoric triamide, dimethylsulfoxide, etc., are also utilizable.

In the practice of the invention, the synthesis mixture, i.e., the final reaction mixture obtained upon trifluoromethylating the halonaphthalene, is first subjected to a replacement of the dipolar aprotic solvent with an alkane containing 6–12, preferably 8–10, carbons and most preferably having a boiling point in the range of $T \pm 30°$ C., where T is the boiling point of the dipolar solvent. The most preferred alkane varies, of course, with the particular dipolar solvent in the mixture but, because of the preference for dimethylformamide and dimethylacetamide as dipolar solvents, is most apt to be octane, nonane, decane, or an alkane mixture having a similar boiling point.

The manner in which the dipolar solvent is replaced is not critical, but it is generally preferred to accomplish the replacement in a manner conducive to easy recycling of the dipolar solvent. Thus, a preferred technique is to remove a large portion, e.g., about 50–70%, of the dipolar solvent from the synthesis mixture by vacuum stripping, add the alkane, and remove the remainder of the dipolar solvent by azeotropic distillation to form a distillate from which the dipolar solvent can be recovered as a separate phase.

After replacement of the dipolar solvent has been completed, the resultant slurry of (trifluoromethyl)naphthalene, unreacted precursors, cuprous iodide, salts, and optional ingredients in an alkane medium is heated to a temperature sufficient to dissolve the organic ingredients, a temperature which is dependent on the amount of alkane medium—lower temperatures, e.g., about 25° C., being sufficient when a considerable excess of alkane is present, and higher temperatures being more suitable when the amount of alkane present is simply compatible with the amount required to disperse the solids. Reflux temperatures are ordinarily preferred.

The inorganic ingredients of the slurry are then allowed to settle, and the organic layer is decanted and cooled to precipitate the (trifluoromethyl)naphthalene. It is then sometimes desirable to repeat the decantation with heated alkane at least one more time to recover the (trifluoromethyl)naphthalene that may have settled with the inorganic ingredients.

When recycle of the cuprous iodide is desired, it may be separated from the water-soluble inorganic ingredients to make it suitable for recycle.

The invention is advantageous as a facile method of recovering (trifluoromethyl)naphthalenes from their synthesis mixtures, while permittng easy recycle of cuprous iodide and dipolar solvent.

The following examples are given to illustrate the invention and are not intended as a limitation thereof.

EXAMPLE I

Part A

A mixture of 8.5 g of 6-methoxy-5-bromo-1-cyanonaphthalene (MBCN), 30 mL of toluene, 12.6 g of cuprous iodide, and 7.44 g of potassium trifluoroacetate was heated to reflux. A 15-mL portion of solvent was distilled. The slurry was then treated with 75 mL of N,N-dimethylformamide (DMF) and heated with solvent distillation until the pot temperature reached 154° C. The mixture was then heated for four hours and then allowed to cool to ambient temperature.

Part B

A 50-mL portion of DMF was distilled off under reduced pressure, a 110-mL portion of n-octane was added, and the remaining DMF was azeotropically distilled. The resulting slurry was warmed to 120° C. and allowed to settle, after which a 90-mL portion of a light brown solution was decanted and set aside to cool.

A fresh 110-mL portion of octane was added to the residue from the first decantation, and a 100-mL dark red portion was decanted and set aside to cool.

Precipitates formed by the cooling of the two decants were separated by filtration of the slurries. The filtrates were concentrated in vacuo; and the precipitates and concentrated mother liquors were all dried at 60° C. in vacuo to afford the following:

| First precipitate | 4.52 g |
| Second precipitate | 1.55 g |
| First mother liquor | 0.42 g |
| Second mother liquor | 0.42 g |

The precipitates were combined and determined by HPLC analysis to have a 6-methoxy-5-trifluoromethyl-1-cyanonaphthalene (MTCN) content of 94%, and the combined mother liquors were determined to have an MTCN content of 55.5%—a combined yield of about 6.2 g (about 77.2%).

EXAMPLE II

Example I was essentially repeated except that the amount of potassium trifluoroacetate employed was 6.45 g.

The amounts of precipitates and concentrated mother liquors afforded after drying in vacuo were:

| First precipitate | 5.00 g |
| Second precipitate | 2.13 g |
| First mother liquor | 0.17 g |
| Second mother liquor | 0.17 g |

HPLC analyses showed the combined precipitates to have an MTCN content of 92% and the combined mother liquors to have an MTCN content of 44%—a combined yield of about 84%.

EXAMPLE III

Part A

A mixture of 8.5 g of MBCN, 30 mL of toluene, 15.6 g of cuprous iodide, and 6.5 g of potassium trifluoroacetate was heated to reflux, and about 15 mL of toluene was distilled over. An addition was made of 75 mL of DMF, and about 15 mL of liquid was distilled over until the temperature reached about 152° C. The reaction mixture was then gently refluxed at about 150°–152° C. for four hours. VPC analysis of the reaction mixture showed an MTCN content of 94.9 area %.

Part B

A 100-mL portion of nonane was added, and about 65 mL of DMF was azeotropically distilled, after which the mixture was refluxed at 149°–150° C. and about 760 mm to remove further DMF. Agitation was discontinued, the cuprous iodide and other salts were allowed to settle, and the hot purple nonane layer was decanted over and set aside to cool.

Another 100 mL of nonane was added, the mixture heated to reflux and allowed to settle, and the hot purple nonane solution decanted and set aside to cool to room temperature.

After the decants stood overnight, solids crystallized and were separated from the mother liquors and dried in a vacuum oven; and the mother liquors were separately evaporated to dryness. FPC analysis showed the MTCN contents to be:

| First precipitate | 97.2% |
| Second precipitate | 97.3% |
| First mother liquor | 65.8% |
| Second mother liquor | 86.2% |

It is obvious that many variations can be made in the products and processes set forth above without departing from the spirit and scope of this invention.

I claim:

1. In a process for preparing a (trifluoromethyl)naphthalene corresponding to the formula:

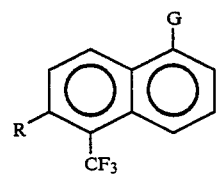

by reacting a halonaphthalene corresponding to the formula:

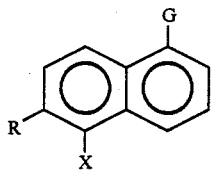

with a sodium, potassium, or tetraalkylammonium trifluoroacetate salt in the presence of cuprous iodide and a dipolar aprotic solvent and recovering the product, R in the formulas representing an alkoxy group containing 1-6 carbons, X representing bromo or iodo, and G representing —CN or —COOR" in which R" is a saturated hydrocarbyl group containing 1-10 carbons, the improvement which comprises recovering the (trifluoromethyl)naphthalene by (1) replacing the dipolar aprotic solvent in the final reaction mixture with an alkane containing 6-12 carbons, (2) heating the resultant slurry to a temperature sufficient to dissolve the organic ingredients, (3) allowing the inorganic ingredients of the slurry to settle, (4) decanting the organic layer, and (5) cooling to precipitate the (trifluoromethyl)naphthalene.

2. The process of claim 1 wherein the (trifluoromethyl)naphthalene is a 6-alkoxy-5-trifluoromethyl-1-cyanonaphthalene.

3. The process of claim 2 wherein the (trifluoromethyl)naphthalene is 6-methoxy-5-trifluoromethyl-1-cyanonaphthalene.

4. The process of claim 1 wherein the dipolar aprotic solvent is an amide selected from N,N-dimethylformamide and N,N-dimethylacetamide.

5. The process of claim 1 wherein the dipolar aprotic solvent is an amide selected from N,N-dimethylformamide and N,N-dimethylacetamide and the alkane is octane, nonane, or decane.

6. The process of claim 1 wherein the trifluoroacetate salt is potassium trifluoroacetate.

7. The process of claim 1 wherein the alkane contains 8-10 carbons.

8. The process of claim 1 wherein the alkane has a boiling point in the range of T±30° C., where T is the boiling point of the dipolar solvent.

9. The process of claim 1 wherein the slurry is heated to reflux temperature before allowing the inorganic ingredients to settle.

10. The process of claim 1 wherein additional alkane is added to the decantation residue to dissolve any remaining organic ingredients, the inorganic ingredients are allowed to resettle, and the organic layer is decanted and cooled.

11. In a process for preparing 6-methoxy-5-trifluoromethyl-1-cyanonaphthalene by reacting 6-methoxy-5-bromo-1-cyanonaphthalene with potassium trifluoroacetate in the presence of cuprous iodide and a dipolar aprotic solvent selected from N,N-dimethylformamide and N,N-dimethylacetamide, the improvement which comprises recovering the product by (1) replacing the amide solvent in the final reaction mixture with an alkane which is selected from octane, nonane, and decane and which has a boiling point in the range of T±30° C., where T is the boiling point of the amide solvent, (2) heating the resultant slurry to reflux temperature, (3) allowing the inorganic ingredients of the slurry to settle, (4) decanting the organic layer and cooling it to precipitate the 6-methoxy-5-trifluoromethyl-1-cyanonaphthalene, (5) adding more hot alkane to the decantation residue to dissolve any remaining organic ingredients, (6) allowing the inorganic ingredients to resettle, and (7) decanting and cooling the organic layer.

* * * * *